United States Patent
Dutton et al.

(10) Patent No.: US 6,810,719 B2
(45) Date of Patent: Nov. 2, 2004

(54) MULTIPHASE FLOW MEASUREMENT SYSTEM

(75) Inventors: Robert E. Dutton, Louisville, CO (US); Chad Steele, Denver, CO (US)

(73) Assignee: Micro Motion, Inc., Boulder, CO (US)

( * ) Notice: Subject to any disclaimer, the term of this patent is extended or adjusted under 35 U.S.C. 154(b) by 0 days.

(21) Appl. No.: 10/358,844

(22) Filed: Feb. 5, 2003

(65) Prior Publication Data

US 2003/0136185 A1 Jul. 24, 2003

Related U.S. Application Data

(63) Continuation of application No. 09/955,765, filed on Sep. 19, 2001, now Pat. No. 6,564,619, which is a continuation of application No. 09/428,416, filed on Oct. 28, 1999, now Pat. No. 6,318,156.

(51) Int. Cl.[7] .............................. G01F 1/74; G01F 15/08
(52) U.S. Cl. .................................... 73/61.44; 73/861.04
(58) Field of Search ........................... 73/61.44, 861.04

(56) References Cited

U.S. PATENT DOCUMENTS

| | | | | |
|---|---|---|---|---|
| 4,429,581 A | * | 2/1984 | Furmaga et al. | 73/861.04 |
| 4,688,418 A | * | 8/1987 | Cheung et al. | 73/29.01 |
| 4,876,897 A | * | 10/1989 | DeCarlo et al. | 73/861.04 |
| 5,127,272 A | * | 7/1992 | Dean et al. | 73/861.04 |
| 5,259,250 A | * | 11/1993 | Kolpak | 73/861.355 |
| 5,400,657 A | * | 3/1995 | Kolpak et al. | 73/861.04 |
| 5,535,632 A | * | 7/1996 | Kolpak | 73/861.04 |
| 5,645,502 A | * | 7/1997 | Wakabayashi et al. | 73/861.04 |
| 6,327,914 B1 | * | 12/2001 | Dutton | 73/861.356 |

* cited by examiner

*Primary Examiner*—Daniel S. Larkin
(74) *Attorney, Agent, or Firm*—Duft Setter Ollila & Bornsen LLC

(57) ABSTRACT

A fully automated Coriolis-based well system which can deliver accurate volumetric flow rate measurements in three phase flow. Measurements are performed according to a process including using N equations and N unknowns technique.

16 Claims, 4 Drawing Sheets

MULTIPHASE FLOW MEASUREMENT SYSTEM

RELATED APPLICATIONS

This application is a continuation of application Ser. No. 09/955,765, filed on Sep. 19, 2001, now U.S. Pat. No. 6,564,619, which is a continuation of application Ser. No. 09/428,416, filed on Oct. 28, 1999, now U.S. Pat. No. 6,318,156, which are hereby incorporated by reference.

BACKGROUND OF THE INVENTION

1. Field of the Invention

The present invention pertains to the field of flow metering technology including a system and method for use in measuring production volumes including a multiphase mixture of discrete phases, e.g., a mixture including oil, gas, and water phases. More specifically, the system and method determine a density of the oil in the multiphase mixture to more efficiently measure a flow rate of the oil.

2. Statement of the Problem

It is often the case that a fluid flowing through a tubular member contains a plurality of phases, i.e., the fluid is a multiphase fluid. As used herein, the term "phase" refers to a type of fluid that may exist in contact with other fluids, e.g., a mixture of oil and water includes a discrete oil phase and a discrete water phase. Similarly, a mixture of oil, gas, and water includes a discrete gas phase and a discrete liquid phase with the liquid phase including an oil phase and a water phase. The term "fluid" is used herein in the context that fluid includes gas and liquids.

Special problems arise when one uses a flowmeter to measure volumetric or mass flow rates in the combined multiphase flow stream. Specifically, the flowmeter is designed to provide a direct measurement of the combined flow stream, but this measurement cannot be directly resolved into individual measurements of the respective phases. This problem is particularly acute in the petroleum industry where producing oil and gas wells provide a multiphase flow stream including unprocessed oil, gas, and saltwater. Commercial markets exist only for the hydrocarbon products.

It is a common practice in the petroleum industry to install equipment that is used to separate respective oil, gas, and water phases of flow from oil and gas wells. The producing wells in a field or a portion of a field often share a production facility for this purpose, including a main production separator, a well test separator, pipeline transportation access, saltwater disposal wells, and safety control features. Proper management of producing oil or gas fields demands knowledge of the respective volumes of oil, gas, and water that are produced from the fields and individual wells in the fields. This knowledge is used to improve the producing efficiency of the field, as well as in allocating ownership of revenues from commercial sales of bulk production.

Early installations of separation equipment have included the installation of large and bulky vessel-type separation devices. These devices have a horizontal or vertical oblong pressure vessel together with internal valve and weir assemblies. Industry terminology refers to a 'two-phase' separator as one that is used to separate a gas phase from a liquid phase including oil and water. The use of a two phase separator does not permit direct volumetric measurements to be obtained from segregated oil and water components under actual producing conditions because the combined oil and water fractions are, in practice, not broken out from the combined liquid stream. A 'three-phase' separator is used to separate the gas from the liquid phases and also separates the liquid phase into oil and water phases. As compared to two-phase separators, three-phase separators require additional valve and weir assemblies, and typically have larger volumes to permit longer residence times of produced materials for gravity separation of the production materials into their respective oil, gas, and water components.

Older pressure vessel separators are bulky and occupy a relatively large surface area. This surface area is very limited and quite expensive to provide in certain installations including offshore production platforms and subsea completion templates. Some development efforts have attempted to provide multiphase measurement capabilities in compact packages for use in locations where surface area is limited. These packages typically require the use of nuclear technology to obtain multiphase flow measurements.

Coriolis flowmeters are mass flowmeters that can also be operated as vibrating tube densitometers. The density of each phase may be used to convert the mass flow rate for a particular phase into a volumetric measurement. Numerous difficulties exist in using a Coriolis flowmeter to identify the respective mass percentages of oil, gas, and water in a total combined flow stream.

U.S. Pat. No. 5,029,482 teaches the use of empirically-derived correlations that are obtained by flowing combined gas and liquid flow streams having known mass percentages of the respective gas and liquid components through a Coriolis meter. The empirically-derived correlations are then used to calculate the percentage of gas and the percentage of liquid in a combined gas and liquid flow stream of unknown gas and liquid percentages based upon a direct Coriolis measurement of the total mass flow rate. The composition of the fluid mixture from the well can change with time based upon pressure, volume, and temperature phenomena as pressure in the reservoir depletes and, consequently, there is a continuing need to reverify the density value.

U.S. Pat. No. 4,773,257 teaches that a water fraction of a total oil and water flow stream may be calculated by adjusting the measured total mass flow rate for water content, and that the corresponding mass flow rates of the respective oil and water phases may be converted into volumetric values by dividing the mass flow rate for the respective phases by the density of the respective phases. The density of the respective phases must be determined from actual laboratory measurements. The '257 patent relies upon separation equipment to accomplish separation of gas from the total liquids, and this separation is assumed to be complete.

U.S. Pat. No. 5,654,502 describes a self-calibrating Coriolis flowmeter that uses a separator to obtain respective oil and water density measurements, as opposed to laboratory density measurements. The oil density measurements are corrected for water content, which is measured by a water cut monitor or probe. The '502 patent relies upon a separator to eliminate gas from the fluids traveling through the meter, and does not teach a mechanism for providing multiphase flow measurements when gas is part of the flow stream that is applied to the Coriolis flowmeter.

U.S. Pat. No. 5,535,532 describes multiple systems that measure the flow rates of oil, gas, and water. The '532 patent calculates the flow rate of oil based on a known or assumed value for the density of oil. One problem with the '532 patent is that none of the described systems calculate or measure the density of oil. The density of oil can be determined by taking a sample of the multiphase flow to a lab, which can be time consuming and expensive. The density of oil can also be assumed from previous data. However, the assumed density may not accurately represent the actual density of the oil.

Even three phase separation equipment does not necessarily provide complete separation of the oil phase from the water phase. Water cut probes are used to measure water content in the segregated oil phase because a residual water content of up to about ten percent typically remains in the visibly segregated oil component. The term 'water cut' is used to describe the water content of a multiphase mixture, and is most often applied to a ratio that represents a relationship between a volume of oil and a volume of water in an oil and water mixture. According to the most conventional usage of the term 'water-cut', well production fluids would have a 95% water-cut when water comprises 95 out of a total 100 barrels of oil and water liquids. The term 'water-cut' is sometimes also used to indicate a ratio of the total volume of oil produced to the total volume of water produced. A term 'oil-cut' could imply the oil volume divided by the combined oil and water volume. As defined herein, the term 'water-cut' encompasses any value that is mathematically equivalent to a value representing water or oil as a percentage of a total liquid mixture including water and oil.

Solution

The present invention helps to solve the above problems that are outlined above by providing a method and system for performing multiphase flow measurements which do not require manual sampling or laboratory analysis of the production fluids in order to determine a density of oil components in the production fluids. The method and system are advantageously cheaper and more efficient than manual sampling. The method and system are also more accurate than prior systems.

One embodiment of the invention comprises a multiphase flow measurement system for performing multiphase flow measurements. The multiphase flow measurement system comprises a separator, a Coriolis flowmeter, a water cut monitor, and a controller. The separator is configured to separate an incoming multiphase flow into a majority liquid component and a majority gas component. The majority liquid component is comprised of a water component and an oil component. The Coriolis flowmeter is configured to receive the majority liquid component and determine a density of the majority liquid component. The water cut monitor is configured to receive the majority liquid component and determine a water cut of the majority liquid component. The controller is configured to communicate with the Coriolis flowmeter and the water cut monitor. The controller is configured to determine if the majority liquid component includes entrained gas. If the majority liquid component is substantially free from entrained gas, then the controller is configured to process the water cut and the density of said majority liquid component to determine a density of the oil component.

In one example, after the controller determines the density of the oil component, then the controller is further configured to measure a flow rate of the oil component based on the density of said oil component. The majority liquid component at this time could include entrained gas.

In another example, the multiphase flow measurement system further comprises a water trap configured to receive the majority liquid component and capture a sample of the water component. A hydrometer in the multiphase flow measurement system is configured to determine the density of the water component from the sample taken by the water trap. The controller is then configured to process the density of the water component, the water cut, and the density of the majority liquid component to determine the density of the oil component.

In another example, the controller looks at the drive gain of the Coriolis flowmeter to determine if the majority liquid component includes entrained gas. The controller first calculates a drive gain of the Coriolis flowmeter. The controller then determines if the drive gain is less than a threshold value. If the drive gain is less than the threshold value, then the majority liquid component does not include entrained gas.

The invention can be further defined by the following aspects. One aspect of the invention is a method of performing multiphase flow measurements in flow environments including a liquid phase and a gas phase, said method comprising:

separating an incoming multiphase flow into a majority liquid component and a majority gas component, said majority liquid component comprising a water component and an oil component;

determining if said majority liquid component includes entrained gas; and if said majority liquid component is substantially free from said entrained gas, then:
  determining a water cut of said majority liquid component;
  determining a density of said majority liquid component using a Coriolis flowmeter; and
  processing said water cut and said density of said majority liquid component to determine a density of said oil component.

Another aspect comprises determining a density of said water component and processing said density of said water component, said water cut, and said density of said majority liquid component to determine said density of said oil component.

Another aspect comprises capturing a sample of said water component using a water trap.

Another aspect comprises measuring said density of said water component from said sample using a hydrometer.

Another aspect comprises separating said incoming multiphase flow into said majority liquid component and said majority gas component using a vortex separator.

Another aspect comprises calculating a drive gain of said Coriolis flowmeter and determining if said drive gain is less than a threshold value.

Another aspect comprises measuring said water cut using a microwave-based monitor.

Another aspect comprises measuring said water cut using a capacitive-based monitor.

Another aspect comprises measuring said water cut using a resistance-based monitor.

Another aspect comprises after determining said density of said oil component, measuring a flow rate of said oil component based on said density of said oil component, wherein said majority liquid component includes said entrained gas.

Another aspect comprises a multiphase flow measurement system for performing multiphase flow measurements in flow environments including a liquid phase and a gas phase, said multiphase flow measurement system comprising:

a separator configured to separate an incoming multiphase flow into a majority liquid component and a majority gas component, said majority liquid component comprising a water component and an oil component;

a Coriolis flowmeter configured to receive said majority liquid component and determine a density of said majority liquid component;

a water cut monitor configured to receive said majority liquid component and determine a water cut of said majority liquid component; and a controller configured to communicate with said Coriolis flowmeter and said water cut monitor, determine if said majority liquid component includes entrained gas, and if said majority liquid component is substantially free from said entrained gas, then said controller is further configured to process said water cut and said density of said majority liquid component to determine a density of said oil component.

Another aspect is that said controller is further configured to receive a density of said water component and process said density of said water component, said water cut, and said density of said majority liquid component to determine said density of said oil component.

Another aspect comprises a water trap configured to receive said majority liquid component and capture a sample of said water component.

Another aspect comprises a hydrometer configured to determine said density of said water component from said sample.

Another aspect is that said separator comprises a vortex separator.

Another aspect is that said controller determines if said majority liquid component includes said entrained gas by being further configured to calculate a drive gain of said Coriolis flowmeter and determine if said drive gain is less than a threshold value.

Another aspect is that said water cut monitor comprises a microwave-based monitor.

Another aspect is that said water cut monitor comprises a capacitive-based monitor.

Another aspect is that said water cut monitor comprises a resistance-based monitor.

Another aspect is that said controller is further configured to measure a flow rate of said oil component based on said density of said oil component, wherein said majority liquid component includes said entrained gas.

Other salient features, objects, and advantages will be apparent to those skilled in the art upon a reading of the discussion below in combination with the accompanying drawings.

DETAILED DESCRIPTION OF THE INVENTION

Figure 1:
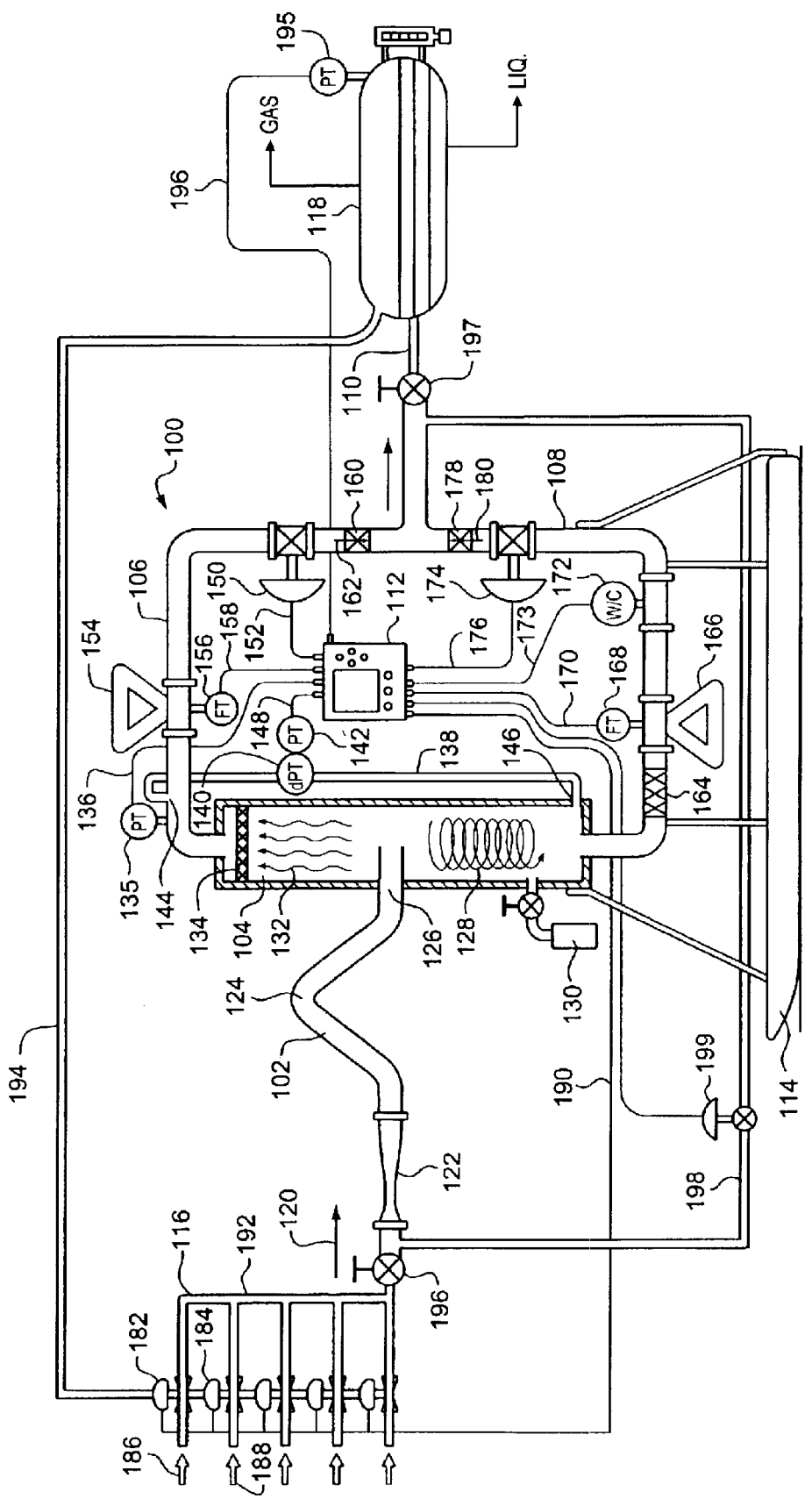
FIG. 1 depicts a schematic layout of an automated well test system according to the present invention.

FIG. 1 depicts a schematic diagram of a compact multiphase flow measurement system 100 for use in the petroleum industry. System 100 includes an incoming multiphase flow line 102 that discharges into a vertical two phase vortex separator 104. In turn, the vortex separator 104 discharges gas into an upper gas measurement flow line 106 and discharges liquids into a lower liquid measurement flow line 108. The gas measurement flow line 106 and the liquid measurement flow line 108 recombine into discharge line 110 after flow measurements have been performed. A controller 112 includes a central processor together with associated circuitry for operating the respective components of system 100. The system 100 is mounted on skid structure 114 for portability, and a production manifold 116 supplies multiphase fluids to system 100 from a plurality of oil or gas wells. Discharge flow line 110 leads to a three phase production separator 118 for separation of gas, water, and oil phases prior to a point of commercial sale.

The incoming multiphase flow line 102 receives multiphase fluids including oil, gas, and water from production manifold 116 along the direction of arrow 120. A venturi section 122 utilizes the well known Bernouli effect to reduce pressure in the incoming multiphase fluids within flow line 102 at the throat of the venturi. It is preferred that the degree of pressure reduction occurs to a level which approximates the internal working pressure within the liquid Coriolis meter 166. This reduction in pressure liberates or flashes gas from the multiphase fluids within flow line 102. An incline/decline section 124 facilitates gravity segregation in the gas and liquid phases of the multiphase fluids preceding the vortex separator 104. A horizontal discharge element 126 feeds the vortex separator 104.

Vortex separator 104 is depicted in midsectional view to reveal interior working components. Discharge element 126 is operably positioned for tangential discharge into the cylindrical interior separation section of vortex separator 104. This manner of discharge causes a tornado or cyclone effect to occur in a liquid portion 128 of multiphase fluids within vortex separator 104.

The liquid portion 128 is a majority liquid phase including discrete water, oil, and entrained gas phases. Centrifugal forces arising from the cyclone effect cause additional separation of the entrained gas phase from the liquid portion 128, but it is not possible to completely eliminate the entrained gas phase except at relatively low flow rates permitting additional gravity segregation of the entrained gas phase. The liquid portion 128 discharges from vortex separator 104 into the liquid measurement flow line 108. A water trap 130 is installed in the lower portion of vortex separator 104. This trap may be bled to obtain periodic water density measurements, or a water density meter (not depicted in FIG. 1) may be installed in combination with the trap 130 to provide water density information to controller 112.

A gas portion 132 of the multiphase fluids within vortex separator is a majority gas phase including gas together with mists of oil and water. A mist collecting screen 134 is used for partial condensation of the mists, which in condensed form drip back into the liquid portion 128

Gas portion 132 discharges into the gas measurement flow line 106. Gas measurement flow line 106 includes a pressure transmitter 135 that transmits an absolute pressure reading of pressure within gas measurement flow line 106 to controller 112 on electrical line 136. Pressure transmitter 135 may be purchased commercially, for example, as a Model 2088 pressure transmitter from Rosemount of Eden Prairie, Minn. A tube 138 connects gas measurement line 106 with the bottom of vortex separator 104. Tube 138 contains a hydrostatic gauge 140 coupled with a pressure transmitter 142 for use in transmitting pressure information concerning the hydrostatic head between point 144 within gas measurement flow line 106 and point 146 at the bottom of vortex separator 104. Electrical line 148 connects the pressure transmitter 142 with controller 112, which uses the hydrostatic head data from pressure transmitter 142 to open and close electrically operable throttling valves 150 and 174 for pressure adjustment assuring proper operation of vortex separator 104, i.e., to prevent vortex separator from becoming overfull with gas to the point where gas portion 132 discharges into liquid measurement flow line 108 or to the point where liquid portion 128 discharges into gas measurement flow line 106. Electrical lines 152 and 176 operably connect controller 112 with the throttling valves 150 and 174, which may, for example, be purchased as Model V2001066-ASCO valves from Fisher of Marshall Town, Iowa.

A Coriolis mass flowmeter 154 in gas measurement flow line 106 provides mass flow rate and density measurements on the gas portion 132 of multiphase fluids within gas measurement flow line 106. The Coriolis mass flowmeter 154 is coupled with a flow transmitter 156 for providing signals representing these measurements to controller 112. Coriolis flowmeter 154 is electronically configured for operations including measurements of mass flow rates, densities, and temperatures of materials passing through gas measurement flow line 106. Exemplary forms of Coriolis flowmeter 154 include the ELITE Models CMF300356NU and Model CMF300H551NU, which are available from Micro Motion of Boulder, Colo.

Electrical line 158 operably couples flow transmitter 156 with controller 112 for transmission of these signals. A check valve 160 in gas measurement flow line 106 assures positive flow in the direction of arrow 162, thus preventing intrusion of liquid portion 128 into gas measurement flow line 106.

Liquid measurement flow line 108 contains a static mixer 164, which turbulates the liquid portion 128 within liquid measurement flow line 108 to prevent gravity segregation of the respective oil, water, and entrained gas phases. A Coriolis flowmeter 166 provides mass flow rate and density measurements of liquid portion 128 within liquid measurement flow line 108, and is connected to flow transmitter 168 for transmission of signals representing these measurements on electrical line 170 to controller 112.

A water cut monitor 172 is installed in liquid measurement flow line 108 to measure the water cut in liquid portion 128 within liquid measurement flow line 108. The type of water-cut monitor is selected depending upon how large the water-cut is expected to be in the flow stream. For example, capacitance meters are relatively inexpensive, but other types of meters may be required where the water-cut may exceed about 30% by volume. Capacitance or resistance probes operate on the principle that oil and water have drastically different dielectric constants. These probes lose sensitivity with increasing water content, and provide acceptably accurate water-cut measurements only where the water volume is less than about 20% to 30% of the total flow stream. The upper 30% accuracy limit is far below the level that is observed from many producing wells. For example, the total liquid production volume of an oil well can be 99% water. Capacitance or resistivity based water-cut monitors, therefore, are relegated to determining the water-cut in an oil component that has a relatively low water content.

Commercially available devices that are used to measure water-cut include near infrared sensors, capacitance/ inductance sensors, microwave sensors, and radio frequency sensors. Each type of device is associated with operational limits. Thus, a water-cut probe can measure the volumetric percentage of water in a combined oil and water flow stream.

Water cut monitoring devices including microwave devices are capable of detecting water in amount up to about one hundred percent of the flow mixture, but in environments including three phase flow are subject to interpreting gas content as oil. This interpretation occurs because microwave detection devices operate on the principle that water in the spectrum of interest absorbs sixty times more microwave energy than does crude oil. The absorption calculations assume is that no natural gas is present, but natural gas absorbs twice as much microwave radiation than does crude oil. It follows that a microwave water cut detection system could correct the water cut reading by compensating for the fact that gas in the mixture has affected the measurement.

Electrical line 173 operably connects water cut monitor 172 with controller 112. Controller 112 uses an electrically actuated two way valve 174 to control pressure in liquid measurement line 108 in a manner that assures proper operation of vortex separator 104 in cooperation with valve 150, i.e., valve 174 is opened and closed to prevent gas portion 132 from discharging into liquid measurement flow line 108 and to prevent liquid portion 128 from discharging into gas measurement flow line 106. Electrical line 176 operably connects valve 174 with controller 112. A check valve 178 in liquid measurement flow line 108 assures positive flow in the direction of arrow 180, thus preventing intrusion of gas portion 132 into the liquid measurement flow line 108. The gas measurement flow line 106 meets in a T with liquid measurement flow line 108 to form a common discharge flow line 110 leading to production separator 118.

Controller 112 is an automation system that is used to govern the operation of system 100. On a basic level, controller 100 includes a computer that is programmed with data acquisition and programming software together with driver circuitry and interfaces for operation of remote devices. A preferred form of controller 112 is the Fisher Model ROC364.

The production manifold 116 contains a plurality of electronically operable three way valves, e.g., valves 182 and 184, which each have corresponding production sources, such as an oil well 186 or a gas well 188. A particularly preferred three way valve for use in this application is the Xomox TUFFLINE 037AX WCB/316 well switching valve with a MATRYX MX200 actuator. The valves are preferably configured to each receive production fluids from a corresponding individual well, but may also receive production from a group of wells. Controller 112 selectively configures these valves by transmitting signals on electrical line 190. The valves are selectively configured to flow multiphase fluids from a well 186 or combinations of wells (e.g. wells 186 and 188) into rail 192 for delivery of fluids into incoming multiphase flow line 102 while other valves are selectively configured to bypass system 100 by flowing through bypass flow line 194.

Production separator 118 is connected to pressure transmitter 195 and an electrical line 196 for transmission of signals to controller 112. Separator 118 is operably connected with a gas sales line, an oil sales line, and a salt water discharge line (not depicted in FIG. 1) in any conventional manner known to those skilled in the art.

Operation of System 100

Figure 2A:
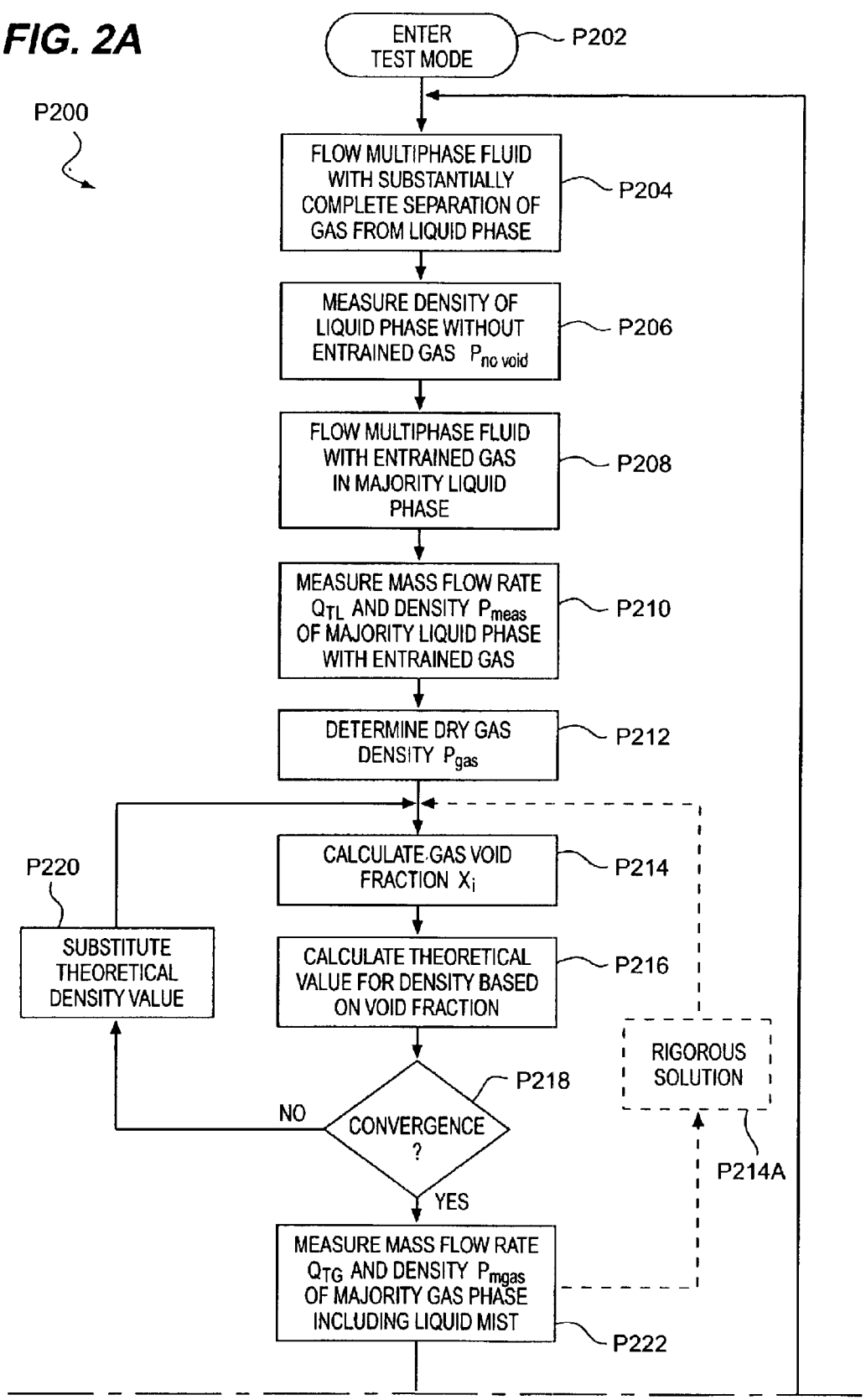
FIGS. 2A and 2B depict a flow chart diagram governing the operation of the FIG. 1 system.
Figure 2B:
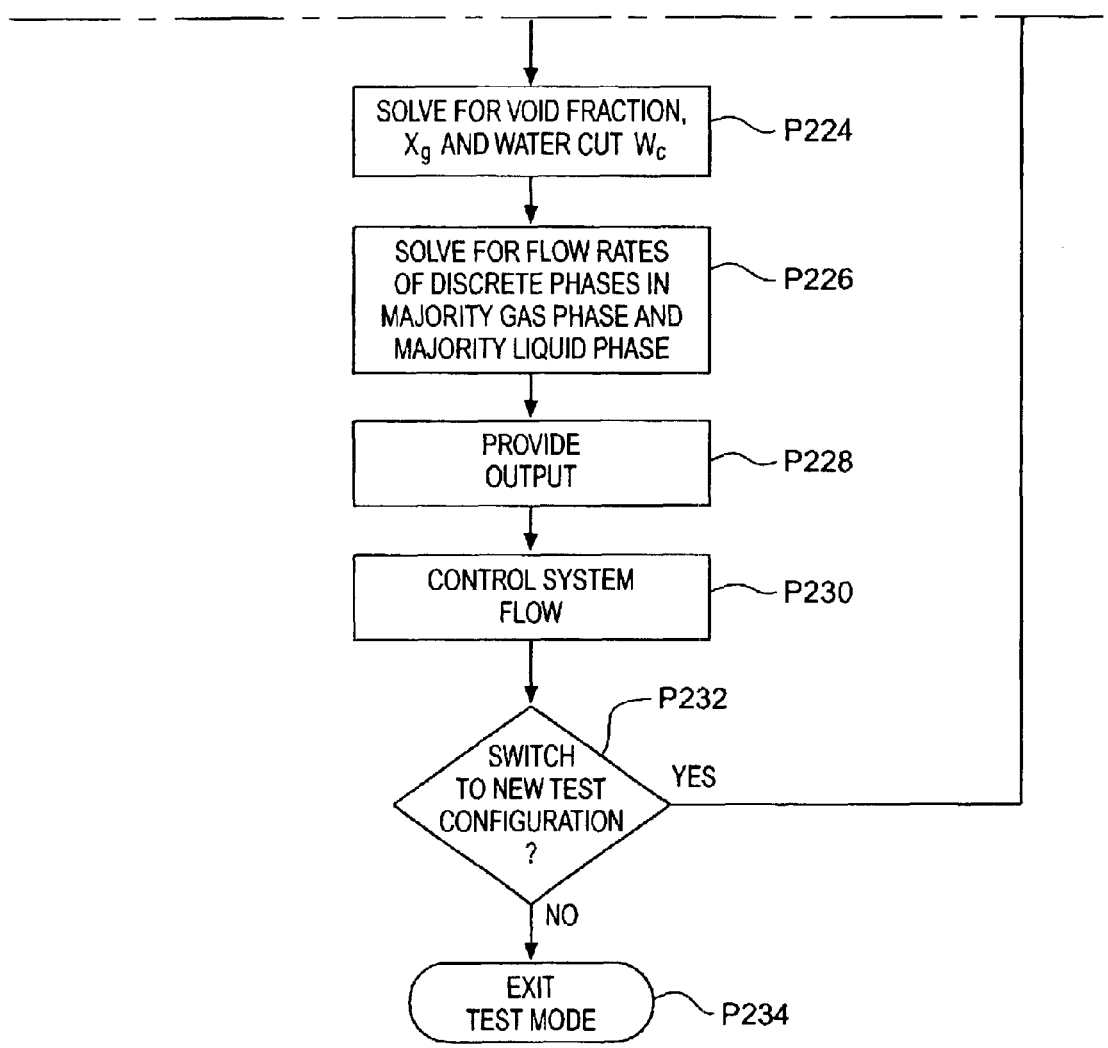

FIGS. 2A and 2B depict a schematic process diagram of a process P200 representing control logic for use in programming controller 112. These instructions typically reside in an electronic memory or an electronic storage device for access and use by controller 112. Instructions that embody the process P200 can be stored on any machine readable medium for retrieval, interpretation, and execution by controller 112 or similar devices that are connected to system 100 in any operable manner.

Process P200 begins with step P202 in which controller 112 determines that it is proper to enter a production test mode. With regard to FIG. 1, this means that controller 112 selectively configures the valves 182 and 184 of production manifold 116 to flow a well or an operator-selected combinations of wells corresponding to production sources 186 and 188 through rail 192 and into incoming multiphase flow line 102. This determination is usually performed on the basis of a time delay, e.g., to test each well at least once per week. The test mode may also be performed on a continuous basis with the respective valves of production manifold 116 always being selectively configured to flow into system 100 while other valves are configured to bypass system 100 through bypass line 194. These types of well test measurements are conventionally used in allocating, on a deliverability basis, the percentages of the total flow stream that pass through production separator 118 to specific production sources, e.g., sources 186 and 188.

Manually actuated valves 196 and 197 can be opened and closed for selective isolation of system 100, i.e., valves 196 and 197 can both be closed for the removal of all components that are mounted on skid 114. An electrically actuated valve 199 is normally closed. A second or redundant bypass line 198 interior to valves 196 and 197 permits flow to bypass system 100 when valve 199 is open and valves 150 and 174 are closed.

Testing begins in step P204 with controller 112 constricting or opening valves 150 and 174 to reduce or increase the total flow rate through vortex separator 104 for the purpose of separating gas from liquid phases in the multiphase fluid. The total flow rate through system 100 need not be reduced because controller 112 can open valve 199 to permit flow through interior bypass 198. The exact flow rate depends upon the physical volume of the vortex separator and liquid measurement flow line 108, as well as the amount of fluid that sources 186 and 188 are capable of delivering to system 100.

The object of reducing the flow rate through system 100 is to eliminate entrained bubbles from liquid measurement flow line 108 through the use of vortex separator 104 with assistance by gravity segregation while the flow rate is still high enough to prevent substantial gravity segregation of oil from water in the remaining liquid phase. It is also possible to accomplish substantially complete separation of the gas phase from the liquid phase by increasing the flow rate with separation being accomplished by centrifugal forces through vortex separator 104. Controller 112 monitors the drive gain or pickoff voltage from Coriolis flowmeter 166 for this purpose, as explained with reference to FIGS. 3 and 4.

Figure 3:
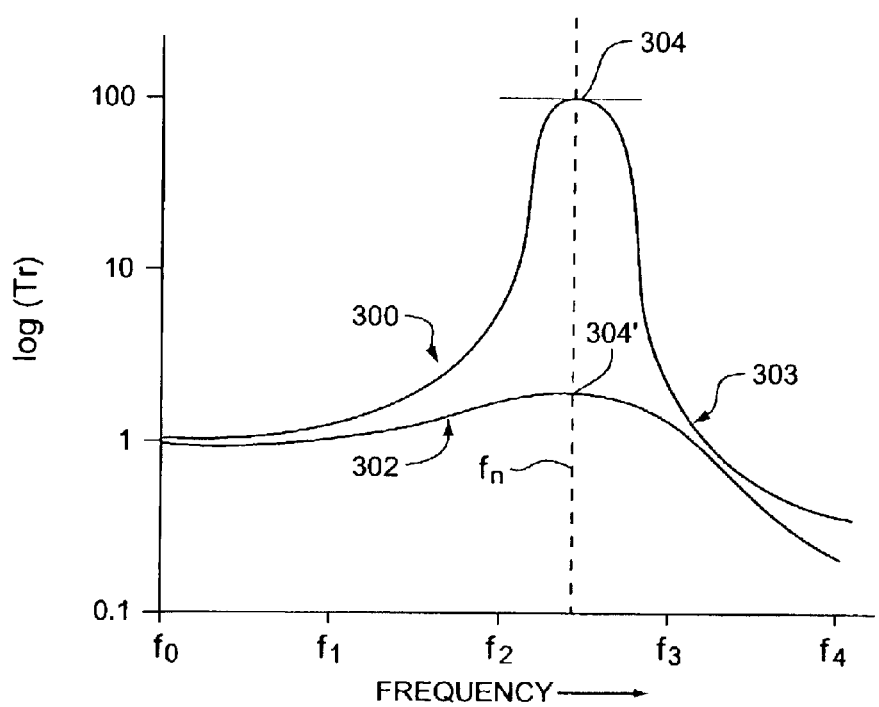
FIG. 3 is a plot of hypothetical data demonstrating the practical effects of gas damping on the frequency response of flowtubes in a Coriolis flowmeter.

FIG. 3 is a plot of hypothetical data demonstrating the practical effects of gas damping on the frequency response of flowtubes in the Coriolis flowmeter 166 (see also FIG. 1). The log of transmissivity is plotted as a function of the frequency of alternating voltage applied to the drive coil of Coriolis flowmeter 166, e.g., at frequencies $f_0$, $f_1$, and $f_2$. The transmissivity ratio $T_r$ equals the output of meter pickoff coils divided by the drive input, i.e., $T_r$ is the drive gain:

$$T_r = \frac{\text{OUTPUT}}{\text{INPUT}} = \frac{V_{ac}\text{PICKOFF COIL}}{V_{ac}\text{DRIVE COIL}} \tag{1}$$

A first curve 300 corresponds to the undamped system of Equation (1), i.e., no gas is present in the fluid being measured. A second curve 302 corresponds to a damped system where gas is present. Both curves 300 and 302 have an optimal value 304 and 304', respectively, at the natural frequency $f_n$.

Figure 4:
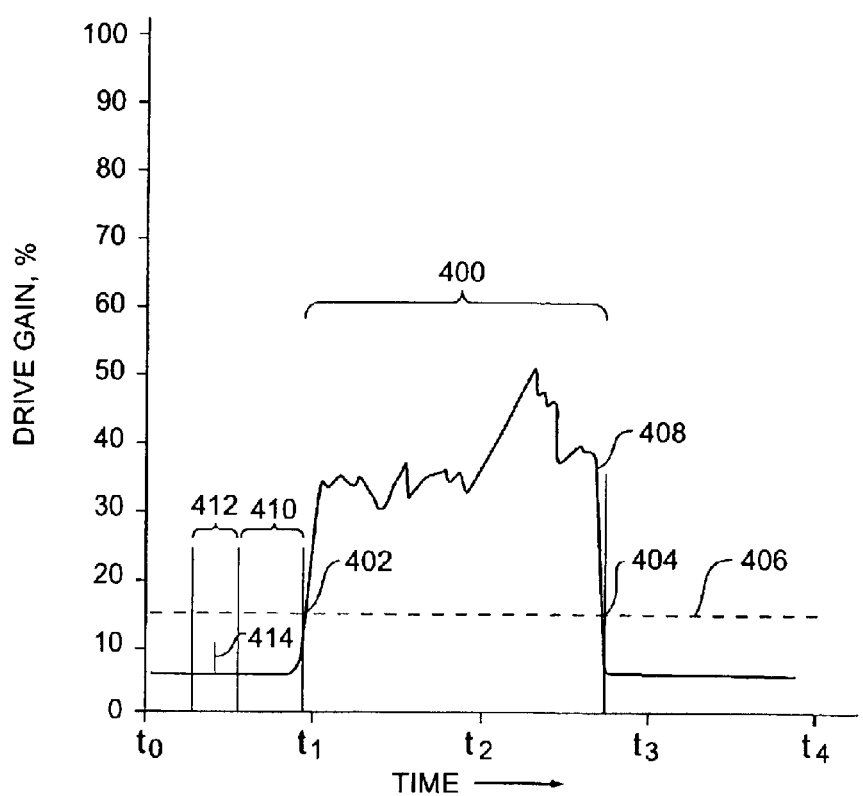
FIG. 4 is a plot of hypothetical data showing the relationship between drive gain and time for an event where a transient bubble enters a Coriolis flowmeter.

FIG. 4 is a plot of hypothetical data showing the relationship between drive gain and time for an event 400 where a transient bubble enters the Coriolis flowmeter 166 as a bubble entrained in a multiphase fluid. The bubble enters at time 402 and exits at time 404. Drive gain is expressed as a percentage in FIG. 4, and plotted as a function of time at intervals, e.g., $t_1$, $t_2$, and $t_3$. Controller 112 (see also FIG. 1) is programmed to monitor drive gain or transmissivity by comparing the same against a threshold value 406. Where the drive gain or transmissivity of curve 408 exceeds threshold 406, controller 112 recognizes that density measurements are affected by the presence of transient bubbles. Thus, Coriolis flowmeter 166 uses only density values obtained when drive gain is less than threshold 406 for purposes of step P206. The exact level of threshold 406 depends upon the specific meter design together with the intended environment of use, and is intended to permit less than one to two percent gas by volume in the multiphase fluid.

In operating Coriolis meters, it is often the case that the pickoff voltage drops in inverse proportion to the event 400 of the curve 408 shown in FIG. 4. The meters are sometimes programmed to sense this drop in amplitude, and they respond by vibrating an oscillation coil to an amplitude of maximum design specification until the gas damping effect is reversed.

With controller 112 opening and/or closing valves 150 and 174 until the drive gain just falls below threshold 406 in the manner described for step P204, step P206 includes Coriolis flowmeter 166 measuring density of the liquid phase without entrained gas. This density measurement is intended to represent density of the liquid phase having no gas voids. This density measurement is referred to as $\rho_L$ in the discussion below, and is used to describe the density of a liquid mixture including gas and oil with no entrained gas fraction. As an alternative to performing direct measurements on the multiphase fluid in liquid measurement line 108, it is also possible to obtain samples of the multiphase fluid for laboratory analysis or to approximate density measurements by the use of empirically derived fluid correlations to obtain less preferred approximations of $\rho_L$.

In step P208, controller 112 selectively adjusts valves 150 and 174 in a manner that optimizes separation results in vortex separator 104 according to manufacturer's specifications based upon the gross rates of flow through Coriolis flowmeters 154 and 166 together with pressure signals received from pressure transmitter 135 and differential pressure gauge 140. In this step, production manifold 116 is configured to flow for active producing well test measurements. Vortex separator 104 functions differently in this step, as compared to step P204, because controller 112 does not adjust valves 150 and 174 in a manner that reduces drive gain below the threshold 406 shown in FIG. 4. In this circumstance, the majority liquid phase flowing through liquid measurement line 108 may include entrained gas bubbles.

Step P210 includes the use of Coriolis flowmeter 166 to measure the total mass flow rate $Q_{TL}$ of the majority liquid phase including entrained gas within liquid measurement line 108, as well as the density of the majority liquid phase. This density measurement is referred to as $\rho_{meas}$ in the discussion that follows.

In step P212, controller 112 determines the dry gas density $\rho_{gas}$ of the gas in the multiphase fluid. Gas density may be calculated from pressure and temperature information using well known correlations developed by the American Gas Association based upon gas gravity, or laboratory analysis may provide other empirical correlations for gas density determined from actual measurements of produced gas from the multiphase flow stream. Another alternative technique for the determination of gas density is to obtain an actual density measurement from Coriolis flowmeter 154 simultaneously with step P204 or in a separate step P210 where controller 112 selectively adjusts valves 150 and 174 to minimize the drive gain intensity shown in FIG. 4. In some situations, it is also possible to assume that the gas density remains constant because the density of gas is relatively low in comparison to the liquid density, and the assumption of a constant gas density may result in an acceptable level of error.

In step P214, controller 112 calculates a gas void fraction $X_L$ in the liquid phase where $$X_{Li} = \frac{\rho_{calc} - \rho_{meas}}{\rho_{calc}},\qquad(2)$$

where $X_{Li}$ is the void fraction representing gas void in the multiphase fluid flowing through Coriolis flowmeter 166, i denotes successive iterations, $\rho_{meas}$ is the density measurement obtained in step P210 as described above, and $\rho_{calc}$ is a calculated or estimated density value approximating the density of a multiphase liquid having a void fraction of about $X_{Li}$. Equation (2) will be used in an iterative convergence algorithm. Thus, it is acceptable to begin calculations with a first guess, e.g., a stored value for $\rho_{calc}$ from the preceding cycle of test measurements for a particular production source 186 or an arbitrary value such as 0.8 g/cc.

A particularly preferred manner of providing a first guess for the value of $\rho_{calc}$ is to obtain a water cut measurement from water cut monitor 172. Then it is possible to assume that no gas is present in the multiphase flow mixture and solve Equation (3) for $\rho_{calc}$:

$$\rho_{calc} = WC(\rho_w - \rho_o) + \rho_o\qquad(3)$$

where WC is water cut expressed as a fraction comprising the amount of water in the liquid mixture divided by the total volume of the liquid mixture, $\rho_w$ is the density of water in the liquid mixture, and $\rho_o$ is the density of oil in the liquid mixture. The resultant first guess for $\rho_{calc}$ is the theoretical value of a liquid mixture having no gas void fraction. The measured density $\rho_{meas}$ will be less than $\rho_{calc}$ when $X_i$ is greater than zero, provided the values $\rho_w$ and $\rho_o$ are correct. The values $\rho_w$ and $\rho_o$ may be obtained from laboratory measurements that are performed on samples of the majority liquid phase including respective oil and water phases. For example, a water density value may be obtained from a hydrometer connected to water trap 130. These values may also be approximated to acceptable levels of accuracy by well known empirical correlations that are published by the American Petroleum Institute.

In step P216, controller 112 performs a calculation to determine whether the last guess for $\rho_{calc}$ has provided a calculation of $X_{Li}$ according to Equation (2) wherein the value of $X_i$ has converged within an acceptable range of error. The next guess for $\rho_{calc}$ is calculated as:

$$\rho_{calci} = (\rho_{gas} X_{Li}) + (1 - X_{Li})\rho_L\qquad(4)$$

where $\rho_{calci}$ is the next guess for $\rho_{calc}$ calculated using the value $X_{Li}$ from Equation (2), $\rho_L$ is the density of the liquid mixture, and the remaining variables are defined above.

Step P218 is a test for convergence wherein convergence exists if the expression:

$$D < |\rho_{calci} - \rho_{calci-1}|\qquad(5)$$

is true where D is the absolute value of a delimiter representing a negligible error, e.g., 0.01 g/cc, or approximating the limits of precision that is available from Coriolis flowmeter 166, $\rho_{calci}$ is the present value calculated according to Equation (4), and $\rho_{calci-1}$ is the old value of $\rho_{calci}$ from the prior iteration of Equation (2) that produced the $X_{Li}$ value corresponding to $\rho_{calci}$.

Where controller 112 in step P218 determines that there is no convergence, the new guess value $\rho_{calci}$ is substituted for the old guess value $\rho_{calci-1}$ in step P220, and steps P214 through P218 are repeated until convergence exists.

Water cut may be calculated as:

$$WC = \frac{\rho_L - \rho_O}{\rho_W - \rho_O}\qquad(6)$$

wherein WC is water cut, $\rho_o$ is a density of oil in the majority liquid component, and $\rho_w$ is a density of water in said majority liquid component. Thus, water cut meter 172 is somewhat redundant if there is no gas phase in the multiphase flow, and may then be optionally eliminated because it is not a required value for this iterative convergence technique.

In step P214A, a more rigorous or noniterative solution is available, provided that the measured water cut value supplied by water cut meter 172 is within a range where the meter functions with acceptable accuracy and precision. The meter reading is a function of the fluid content, and this permits the simultaneous solution of a system of three equations to provide answers for three variables where the equations are:

$$\rho_w q_w + \rho_o q_o + \rho_g q_g = \rho_{mix},\qquad(7)$$

$$f(sat) = M\qquad(8)$$

$$q_w + q_o + q_g = 1\qquad(9)$$

where $\rho_w$ is the density of water in the flow stream, $\rho_o$ is the density of oil in the flow stream, $\rho_g$ is the density of gas in the flow stream, $\rho_{mix}$ is the density of the combined flow stream, $q_w$ is the fractional flow rate of water by volume (i.e., a water-cut), $q_0$ is the fractional flow rate of oil by volume, $q_g$ is the fractional flow rate of gas by volume, and $f(sat)$ is a function of flow stream content that is unique to a particular type of water-cut meter providing a total meter reading M.

Where the water-cut meter is a microwave meter, the function $f(sat)=M$ may be approximated as:

$$m_w q_w + m_o q_o + m_g g = M,\qquad(10)$$

where $m_w$ is the meter reading in pure water, $m_o$ is the meter reading in pure oil, $m_g$ is the meter reading in pure gas, and the remaining terms are described above. Where, in a typical meter, $m_w=60$, $m_o=1$, and $m_g=2$, Equations (8) through (11) can be solved for $q_w$ as:

$$q_w = \frac{(\rho_{mix} - \rho_o) - (M-1)(\rho_g - \rho_o)}{(\rho_w - \rho_o) - 59(\rho_g - \rho_o)} \quad (11)$$

where the terms are defined above. Also, $$q_g = M - 1 - 59q_w, \text{ and} \quad (12)$$

$$q_o = 58q_w - M + 2. \quad (13)$$

Once convergence is achieved in step P218, step P222 entails using Coriolis flowmeter 154 to measure the mass flow rate $Q_{TG}$ and density $\rho_{mgas}$ of the majority gas phase flowing through Coriolis flowmeter 154 under the flow conditions of step P208.

Step P224, as shown in FIG. 2B, includes solving for the gas void fraction $X_G$ in the majority gas phase flowing through gas measurement line 106, according to the equation:

$$XG = \frac{\rho_{mgas} - \rho_L}{\rho_{gas} - \rho_L} \quad (14)$$

where $X_G$ is a fraction corresponding to a volume of gas taken with respect to the total volume of the majority gas phase, $\rho_{mgas}$ is a value obtained in step P222, $\rho_{gas}$ is a value obtained in step P212, and $\rho_L$ is a value obtained in step P206.

In step P224, the value of water cut obtained from water cut monitor 172 is adjusted, as needed, to compensate for the presence of gas in the majority liquid phase. For example, where the gas void fraction $X_{Li}$ is known, it is possible to use this value to correct water cut readings for microwave absorption based upon the assumption that only oil and water are present.

Step P226 includes using the data thus acquired to solve for the flow rates of the three respective phases in each of the majority liquid phase and the majority gas phase. These equations are useful for this purpose:

$$Q_L = Q_{TL}*(1-Xi) + Q_{TG}*(1-X_G); \quad (15)$$

$$Q_G = Q_{TL}*Xi*Q_{TG}*X_G; \quad (16)$$

$$Q_O = Q_L*(1-WC); \quad (17)$$

$$Q_W = Q_L*WC; \quad (18)$$

$$V_L = \frac{Q_L}{P_L}; \quad (19)$$

$$V_o = \frac{Q_o}{P_o}; \quad (20)$$

$$V_G = \frac{Q_G}{P_o}; \text{ and} \quad (21)$$

$$V_W = \frac{Q_W}{P_W}, \quad (22)$$

wherein $Q_L$ is the total mass flow rate of the liquid phases flowing through system 100; $Q_{TL}$ is the total mass flow rate of the majority liquid phase including entrained gas; $X_i$ is the gas void fraction in the majority liquid phase determined from step P214 and resulting in convergence in step P218; $Q_{TG}$ is the total gas mass flow rate of the majority gas phase measured in step P222; $X_G$ is the gas void fraction in the majority gas phase determined in step P224; $Q_G$ is the total gas mass flow rate through system 100; $Q_O$ is the total oil mass flow rate through system 100; $Q_W$ is the total water mass flow rate through system 100; WC is the water cut provided from water cut monitor 172 with corrections as needed in step P224; $V_L$ is the total volumetric flow rate of the liquid phases flowing through system 100; $\rho_L$ is the liquid phase density determined in step P206; $V_O$ is the total oil volumetric flow rate through system 100; $\rho_o$ is oil density at flow conditions; $V_G$ is the total gas volumetric flow rate through system 100; $\rho_{gas}$ is gas density at flow conditions; $V_w$ is the total water volumetric flow rate through system 100; and $\rho_W$ is water density at flow conditions.

Controller 112 in step P228 provides system outputs including direct temperature, density, and mass flow rate measurements together with calculation results for volumetric and mass flow rates for the respective phases. These flow rates may be integrated over time to provide cumulative production volumes for the test interval.

Controller 112 in step P230 interacts with system components including production manifold 116 to optimize field efficiency. For example, in an oilfield having drive energy that is predominated by a gas cap, production efficiency is optimized when the gas cap is depleted after the oil is recovered. It is desirable to produce oil referentially before the gas, and the gas-oil contact may move downward into the former oil zone as the oil is depleted. This movement of the gas-oil contact can result in wells that formerly produced primarily oil changing to produce primarily gas. The proper response to this drastically increased gas production in an oil well is normally to shut the well in or reduce its production rate so as not to deplete the drive energy of the reservoir, and controller 112 can be programmed to take this action. Similar responses can be programmed for moving oil-water contacts or even to optimize present economic performance from an accounting standpoint by producing one low cost well before higher cost wells if all other factors are equal.

In step P232, controller 112 determines if a new test configuration should be executed. If controller 112 determines that a new test configuration should be executed, then controller 112 returns to step P204. If controller 112 determines that a new test configuration should not be executed, then controller 112 exits the production test mode in step P234.

Those skilled in the art understand that the preferred embodiments described hereinabove may be subjected to apparent modifications without departing from the scope and spirit of the invention. Accordingly, the inventors hereby state their full intention to rely upon the Doctrine of Equivalents in order to protect their full rights in the invention.

What is claimed is:

1. A method of performing multiphase flow measurements in a multiphase flow stream including liquid and gas components, said method comprising:
   determining a mass flow rate and density of said multiphase flow stream using a Coriolis flow meter; and
   calculating to quantify flow rates of discrete liquid and gas components, said calculating comprises solving the following equations:

$$\rho_g q_o + \rho_w q_w + \rho_g q_g = \rho_{MIX}$$

$$\eta(\text{sat}) = M$$

$$q_q + q_w + q_g = 1$$

wherein $\rho_w$ is the density of water in the flow stream, $\rho_o$ is the density of oil in the flow stream, $\rho_o$ is the density of gas in the flow stream, $\rho_{MIX}$ is the density of the combined flow stream, $q_w$ is the fractional flow rate of water by volume (i.e., a water-cut), $q_o$ is the fractional flow rate of oil by volume, $q_g$ is the fractional flow rate of gas by volume, and $\eta(sat)$ is a function of flow stream content that is unique to a particular type of water-cut meter providing a total meter reading M.

2. The method of claim 1 wherein the values of $\rho_w$, $\rho_o$, and $\rho_g$ are obtained from laboratory measurements or based upon temperature and pressure information using correlations from an industry standards group.

3. The method of claim 1 wherein $\eta(sat)$ operates according to the relationship:

$$m_w q_w + m_o q_o + m_g q_g = M$$

wherein $m_w$ is the meter reading in pure water, $m_o$ is the meter reading in pure oil, and $m_g$ is the meter reading in pure gas.

4. The method of claim 1 wherein determining said water cut of said multiphase flow stream comprises:
  measuring said water cut using a microwave-based monitor.

5. A method of performing multiphase flow measurements in a multiphase flow stream including liquid and gas components, said method comprising:
  determining a mass flow rate and density of said multiphase flow stream using a Coriolis flow meter:
  calculating to quantify flow rates of discrete liquid and gas components, said calculation comprising solving N equations with N unknowns:
  determining a temperature of said multiphase flow;
  determining a pressure of said multiphase flow; and
  correcting said flow rate of said discrete liquid component to a standard volume flow rate using said temperature measurement, said pressure, and correlations obtained from an industry standards group.

6. A method of performing multiphase flow measurements in a multiphase flow stream including liquid and gas components, said method comprising:
  determining a mass flow rate and density of said multiphase flow stream using a Coriolis flow meter:
  calculating to quantify flow rates of discrete liquid and gas components, said calculation comprising solving N equations with N unknowns:
  determining a temperature of said multiphase flow;
  determining a pressure of said multiphase flow; and
  correcting said flow rate of said discrete gas component to a standard volume flow rate using said temperature measurement, said pressure, and correlations obtained from an industry standards group.

7. A multiphase flow stream measurement system for use in flow streams including multiple liquid components and a gas component comprising:
  means for measuring a mass flow rate and density of said multiphase flow stream; and
  means for measuring a flow rate of said liquid and gas components, wherein said means for measuring a flow rate of said liquid and gas components uses a calculation to quantify flow rates of discrete liquid and gas phases in said multiphase flow stream, said calculation comprises solving the following equations:

$$\rho_g q_o + \rho_w q_w + \rho_g q_g = \rho_{MIX}$$

$$\eta(sat) = M$$

$$q_q + q_w + q_g = 1$$

wherein $\rho_w$ is the density of water in the flow stream, $\rho_o$ is the density of oil in the flow stream, $\rho_g$ is the density of gas in the flow stream, $\rho_{MIX}$ is the density of the combined flow stream, $q_w$ is the fractional flow rate of water by volume (i.e., a water-cut), $q_g$ is the fractional flow rate of oil by volume, $q_g$ is the fractional flow rate of gas by volume, and $\eta(sat)$ is a function of flow stream content that is unique to a particular type of water-cut meter providing a total meter reading M.

8. The multiphase flow measurement system of claim 7 wherein said means for measuring a mass flow rate of said multiphase flow stream comprises a mass flowmeter.

9. The multiphase flow measurement system of claim 8 wherein said mass flowmeter is a Coriolis mass flowmeter.

10. The multiphase flow measurement system of claim 7 wherein $\eta(sat)$ operates according to the relationship:

$$m_w q_w + m_o q_o + m_g q_g = M$$

wherein $m_w$ is the meter reading in pure water, $m_o$ is the meter reading in pure oil, and $m_g$ is the meter reading in pure gas.

11. A multiphase flow stream measurement system for use in flow streams including multiple liquid components and a gas component comprising:
  means for measuring a mass flow rate and density of said multiphase flow stream:
  means for measuring a flow rate of said liquid and gas components, wherein said means for measuring a flow rate of said liquid and gas components uses a calculation to quantify flow rates of discrete liquid and gas phases in said multiphase flow stream, said calculation comprising solving N equations with N unknowns:
  means for determining a temperature of said multiphase flow:
  means for determining a pressure of said multiphase flow; and
  means for correcting said flow rate of said liquid and gas components to a standard volume flow rate using said temperature measurement, said pressure measurement and correlations obtained from an industry standards group.

12. The multiphase flow measurement system of claim 11 wherein said means for determining said temperature is a Coriolis flowmeter and said means for determining said pressure is a pressure transmitter.

13. A multiphase flow measurement system for performing multiphase flow measurements in flow streams including multiple liquid phases and a gas phase, said multiphase flow measurement system comprising:
  a flowmeter configured to receive said multiphase flow and determine a flow rate and a density of said multiphase flow;
  a water cut monitor configured to receive said multiphase flow and determine a water cut of said multiphase flow; and
  a controller configured to communicate with said flowmeter and said water cut monitor, for measuring a flow rate of said liquid and gas components, wherein said controller uses a calculation to quantify flow rates of discrete liquid and gas phases in said multiphase flow stream, said calculation comprises solving the following equations:

$$\rho_g q_o + \rho_w q_w + \rho_g q_g = \rho_{MIX}$$

$$\eta(sat) = M$$

$$q_q + q_w + q_g = 1$$

wherein $\rho_w$ is the density of water in the flow stream, $\rho_o$ is the density of oil in the flow stream, $\rho_g$ is the density of gas in the flow stream, $\rho_{MIX}$ is the density of the combined flow stream, $q_w$ is the fractional flow rate of water by volume (i.e., a water-cut), $q_o$ is the fractional flow rate of oil by volume, $q_g$ is the fractional flow rate of gas by volume, and η(sat) is a function of flow stream content that is unique to a particular type of water-cut meter providing a total meter reading M.

14. The multiphase flow measurement system of claim 13 wherein said flowmeter comprises a Coriolis mass flowmeter.

15. The multiphase flow measurement system of claim 13 wherein η(sat) operates according to the relationship:

$$m_w q_w + m_o q_o + m_g q_g = M$$

wherein $m_w$ is the meter reading in pure water, $m_o$ is the meter reading in pure oil, and $m_o$ is the meter reading in pure gas.

16. A multiphase flow measurement system for performing multiphase flow measurements in flow streams including multiple liquid phases and a gas phase, said multiphase flow measurement system comprising:

a flowmeter configured to receive said multiphase flow and determine a flow rate and a density of said multiphase flow:

a water cut monitor configured to receive said multiphase flow and determine a water cut of said multiphase flow:

a controller configured to communicate with said flowmeter and said water cut monitor, for measuring a flow rate of said liquid and gas components, wherein said controller uses a calculation to quantity flow rates of discrete liquid and gas phases in said multiphase flow stream, said calculation comprising solving N equations with N unknowns:

a pressure transmitter for determining a pressure of said multiphase flow; and means for correcting said flow rate of said liquid and gas components to a standard volume flow rate using said temperature, said pressure, and correlations obtained from an industry standards group.

* * * * *

UNITED STATES PATENT AND TRADEMARK OFFICE
CERTIFICATE OF CORRECTION

PATENT NO. : 6,810,719 B2
DATED : November 2, 2004
INVENTOR(S) : Robert E. Dutton and Chad Steele It is certified that error appears in the above-identified patent and that said Letters Patent is hereby corrected as shown below:

Column 4,
Line 16, cancel the text beginning with "The invention can be further" to ending "said entrained gas." in Column 5, line 44, and insert the following text:

--The invention can be further defined by the following aspects. One aspect of the invention is a method of performing multiphase flow measurements in a multiphase flow stream including liquid and gas components, said method comprising:
  determining a mass flow rate and density of said multiphase flow stream using a Coriolis flow meter; and
  calculating to quantify flow rates of discrete liquid and gas components, said calculation comprising solving N equations with N unknowns.
    Another aspect is that said N equations with said N unknowns comprise:
$$\rho_o q_o + \rho_w q_w + \rho_g q_g = \rho_{mix}$$
$$f(sat) = M$$
$$q_o + q_w + q_g = 1$$
wherein $\rho_w$ is the density of water in the flow stream, $\rho_o$ is the density of oil in the flow stream, $\rho_g$ is the density of gas in the flow stream, $\rho_{mix}$ is the density of the combined flow stream, $q_w$ is the fractional flow rate of water by volume (i.e., a water-cut), $q_o$ is the fractional flow rate of oil by volume, $q_g$ is the fractional flow rate of gas by volume, and f(sat) is a function of flow stream content that is unique to a particular type of water-cut meter providing a total meter reading M.
    Another aspect is that the values of $\rho_w$, $\rho_o$, and $\rho_g$ are obtained from laboratory measurements or based upon temperature and pressure information using correlations from an industry standards group.
    Another aspect is that f(sat) operates according to the relationship:
$$m_w q_w + m_o q_o + m_g q_g = M$$
wherein $m_w$ is the meter reading in pure water, $m_o$ is the meter reading in pure oil, and $m_g$ is the meter reading in pure gas.
    Another aspect comprises determining said water cut of said multiphase flow stream comprising measuring said water cut using a microwave-based monitor.
Another aspect comprises determining a temperature of said multiphase flow, determining a pressure of said multiphase flow, and correcting said flow rate of said discrete liquid component to a standard volume flow rate using said temperature measurement, said pressure, and correlations obtained from an industry standards group.
Another aspect comprises determining a temperature of said multiphase flow, determining a pressure of said multiphase flow, and correcting said flow rate of said discrete gas component to a standard volume flow rate using said temperature measurement, said pressure, and correlations obtained from an industry standards group.
Another aspect comprises a multiphase flow stream measurement system for use in flow streams including multiple liquid components and a gas component comprising:
  means for measuring a mass flow rate and density of said multiphase flow stream; and
  means for measuring a flow rate of said liquid and gas components, wherein said means for measuring a flow rate of said liquid and gas components uses a calculation to quantify flow rates of discrete liquid and gas phases in said multiphase flow stream, said calculation comprising solving N equations with N unknowns.
    Another aspect is that said means for measuring a mass flow rate of said multiphase flow stream comprises a mass flowmeter.
    Another aspect is that said mass flowmeter is a Coriolis mass flowmeter.
    Another aspect is that said N equations with N unknowns comprise:
$$\rho_o q_o + \rho_w q_w + \rho_g q_g = \rho_{mix}$$
$$f(sat) = M$$
$$q_o + q_w + q_g = 1$$
wherein $\rho_w$ is the density of water in the flow stream, $\rho_o$ is the density of oil in the flow stream, $\rho_g$ is the density of gas in the flow stream, $\rho_{mix}$ is the density of the combined flow stream, $q_w$ is the fractional flow rate of water by volume (i.e., a water-cut), $q_o$ is the fractional flow rate of oil by volume, $q_g$ is the fractional flow rate of gas by volume, and f(sat) is a function of flow stream content that is unique to a particular type of water-cut meter providing a total meter reading M.
    Another aspect is that f(sat) operates according to the relationship:
$$m_w q_w + m_o q_o + m_g q_g = M$$
wherein $m_w$ is the meter reading in pure water, $m_o$ is the meter reading in pure oil, and $m_g$ is the meter reading in pure gas.
    Another aspect comprises means for determining a temperature of said multiphase flow, means for determining a pressure of said multiphase flow, and means for correcting said flow rate of said discrete components to a standard volume flow rate using said temperature measurement, said pressure measurement and correlations obtained from an industry standards group.
    Another aspect is that said means for determining said temperature is a Coriolis flowmeter and said means for determining said pressure is a pressure transmitter.
    Another aspect comprises a multiphase flow measurement system for performing multiphase flow measurements in flow streams including multiple liquid phases and a gas phase, said multiphase flow measurement system comprising:
  a flowmeter configured to receive said multiphase flow and determine a flow rate and a density of said multiphase flow;
  a water cut monitor configured to receive said multiphase flow and determine a water cut of said multiphase flow; and

UNITED STATES PATENT AND TRADEMARK OFFICE
CERTIFICATE OF CORRECTION

PATENT NO. : 6,810,719 B2
DATED : November 2, 2004
INVENTOR(S) : Robert E. Dutton and Chad Steele It is certified that error appears in the above-identified patent and that said Letters Patent is hereby corrected as shown below:

Column 4, (cont.)

a controller configured to communicate with said flowmeter and said water cut monitor, for measuring a flow rate of said liquid and gas components, wherein said controller uses a calculation to quantify flow rates of discrete liquid and gas phases in said multiphase flow stream, said calculation comprising solving N equations with N unknowns.
Another aspect is that said flowmeter comprises a Coriolis mass flowmeter.
Another aspect is that said N equations with N unknowns comprise:

$$\rho_o q_o + \rho_w q_w + \rho_g q_g = \rho_{MIX}$$
$$f(sat) = M$$
$$q_o + q_w + q_g = 1$$

wherein $\rho_w$ is the density of water in the flow stream, $\rho_o$ is the density of oil in the flow stream, $\rho_g$ is the density of gas in the flow stream, $\rho_{MIX}$ is the density of the combined flow stream, $q_w$ is the fractional flow rate of water by volume (i.e., a water-cut), $q_o$ is the fractional flow rate of oil by volume, $q_g$ is the fractional flow rate of gas by volume, and f(sat) is a function of flow stream content that is unique to a particular type of water-cut meter providing a total meter reading M.
Another aspect is that f(sat) operates according to the relationship:

$$m_w q_w + m_o q_o + m_g q_g = M$$

wherein $m_W$ is the meter reading in pure water, $m_o$ is the meter reading in pure oil, and $m_g$ is the meter reading in pure gas.
Another aspect is that said flowmeter is configured to measure a temperature of said multiphase flow and said system further comprises a pressure transmitter for determining a pressure of said multiphase flow, and means for correcting said flow rate of said discrete components to a standard volume flow rate using said temperature, said pressure, and correlations obtained from an industry standards group.--

Column 12,
Formula (10), that portion of the formula reading "$m_{gg}$" should read -- $m_g q_g$ --.

Column 13,
Formula (14), that portion of the formula reading "XG" should read -- $X_G$ --.

Column 14,
Lines 59-63, cancel the three equations and replace them with the following Three equations:

$$\rho_o q_o + \rho_w q_w + \rho_g q_g = \rho_{MIX}$$
-- $$f(sat) = M$$ --;
$$q_o + q_w + q_g = 1$$

Line 65, "$\rho_o$" should be changed to -- $\rho_g$ --.

Column 15,
Lines 3, 10 and 66, each occurrence of "$\eta(sat)$" should be changed to -- $f(sat)$ --;
Line 6, "$\rho_w$." should be changed to -- $\rho_w$, --.
Lines 26, 29, 41 and 44, each occurrence of ":" should be changed to ";";
Line 64, the portion of the equation reading "$\rho_g q_o$" should read -- $\rho_o q_o$ --;
Line 68, the portion of the equation reading "$q_q$" should read -- $q_o$ --.

UNITED STATES PATENT AND TRADEMARK OFFICE
CERTIFICATE OF CORRECTION

PATENT NO. : 6,810,719 B2
DATED : November 2, 2004
INVENTOR(S) : Robert E. Dutton and Chad Steele It is certified that error appears in the above-identified patent and that said Letters Patent is hereby corrected as shown below:

Column 16,
Line 5, "$q_g$" should read -- $q_o$ --;
Lines 6, 16 and 68, each occurrence of "$\eta(sat)$" should be changed to -- $f(sat)$ --;
Lines 27, 33 and 35, each occurrence of ":" should be changed to -- ; --;
Line 66, the portion of the equation reading "$\rho_g q_o$" should read -- $\rho_o q_o$ --.

Column 17,
Line 1, the portion of the equation reading "$q_q$" should read -- $q_o$ --;
Lines 9 and 16, each occurrence of "$\eta(sat)$" should be changed to -- $f(sat)$ --;
Line 21, "$m_o$" should read -- $m_g$ --.

Column 18,
Lines 6, 8 and 15, each occurrence of ":" should be changed to -- ; --;
Line 12, "quantity" should read -- quantify --.

Signed and Sealed this

Fourteenth Day of June, 2005

JON W. DUDAS
*Director of the United States Patent and Trademark Office*